(12) United States Patent
Orosco et al.

(10) Patent No.: US 11,094,404 B2
(45) Date of Patent: Aug. 17, 2021

(54) ELECTRONIC MEDICAL RECORD INTEGRATION

(71) Applicant: INTEROPERABILITY BIDCO, INC, Boston, MA (US)

(72) Inventors: John Orosco, Johnston, IA (US); Jeremy E. Pierotti, Minneapolis, MN (US); David Sansom, Chicago, IL (US)

(73) Assignee: INTEROPERABILITY BIDCO, INC, Boston, MA (US)

( * ) Notice: Subject to any disclaimer, the term of this patent is extended or adjusted under 35 U.S.C. 154(b) by 176 days.

(21) Appl. No.: 15/779,259

(22) PCT Filed: Dec. 7, 2016

(86) PCT No.: PCT/US2016/065432
§ 371 (c)(1),
(2) Date: May 25, 2018

(87) PCT Pub. No.: WO2017/100352
PCT Pub. Date: Jun. 15, 2017

(65) Prior Publication Data
US 2018/0350452 A1 Dec. 6, 2018

Related U.S. Application Data

(60) Provisional application No. 62/264,714, filed on Dec. 8, 2015.

(51) Int. Cl.
*G16H 10/60* (2018.01)
*G16H 40/20* (2018.01)
(Continued)

(52) U.S. Cl.
CPC ............. *G16H 10/60* (2018.01); *G06F 16/86* (2019.01); *G06F 16/986* (2019.01); *G16H 40/20* (2018.01)

(58) Field of Classification Search
CPC ........ G16H 10/60; G16H 40/20; G06F 16/86; G06F 16/986
See application file for complete search history.

(56) References Cited

U.S. PATENT DOCUMENTS 7,752,035 B2   7/2010   Oon
8,583,694 B2   11/2013  Siegel et al.
(Continued)

FOREIGN PATENT DOCUMENTS

WO   2015/137703 A1   9/2015

OTHER PUBLICATIONS

International Pat. App. No. PCT/US2016/065432, International Search Report and Written Opinion dated Feb. 17, 2017, 10 pages.
(Continued)

*Primary Examiner* — Michael Tomaszewski
*Assistant Examiner* — Mohmad Muqueeth
(74) *Attorney, Agent, or Firm* — Mintz Levin Cohn Ferris Glovsky and Popeo, P.C.

(57) ABSTRACT

Techniques for electronic medical record (EMR) integration are described. A middleware application may receive a command from a third-party application via an electronic network. The command may conform to a unified data format specified by a unified data model. The command may include a request to retrieve data from or write data to an EMR system. The middleware application may convert, using a mapping registrar, the command into a data format compatible with the EMR system. The middleware application may transmit, via another electronic network, the converted command to the EMR system. The middleware application may receive a response from the EMR system. The middleware application may convert, using a mapping registrar, the response into a result that may conform to the
(Continued)

unified data format. The middleware application may transmit the converted result to the third-party application.

21 Claims, 6 Drawing Sheets

(51) Int. Cl.
*G06F 16/84* (2019.01)
*G06F 16/958* (2019.01)

(56) References Cited

U.S. PATENT DOCUMENTS

| | | | |
|---|---|---|---|
| 8,650,045 B2 | 2/2014 | Baldock et al. | |
| 8,918,385 B1 | 12/2014 | Ansari et al. | |
| 9,996,664 B2 | 6/2018 | Lloyd et al. | |
| 2007/0016450 A1* | 1/2007 | Bhora | G16H 10/60 |
| | | | 705/3 |
| 2011/0178821 A1* | 7/2011 | Smith | G06Q 50/24 |
| | | | 705/3 |
| 2012/0215560 A1 | 8/2012 | Ofek et al. | |
| 2013/0030838 A1 | 1/2013 | Myers et al. | |
| 2013/0185087 A1 | 7/2013 | Merkin | |
| 2014/0249854 A1 | 9/2014 | Moore | |
| 2015/0088549 A1* | 3/2015 | Moore | G16H 10/60 |
| | | | 705/3 |

OTHER PUBLICATIONS

Julie Creswell, "Doctors Find Barriers to Sharing Digital Medical Records," The New York Times (http://nyti.ms/Zo1Tuk) Sep. 30, 2014, 5 pages.

* cited by examiner

ELECTRONIC MEDICAL RECORD INTEGRATION

PRIORITY CLAIM

This application is a 35 U.S.C. 371 national phase filing from International Application No. PCT/US2016/065432, filed Dec. 7, 2016, which claims priority to U.S. Provisional Application No. 62/264,714, filed Dec. 8, 2015. The entire contents of both these applications are incorporated herein by reference.

TECHNICAL FIELD

This disclosure generally relates to integrating and querying disparate and incompatible electronic medical records and producing compiled search results.

BACKGROUND

Health care providers commonly choose from among several major systems for creating and storing their electronic medical records ("EMR"). For various reasons, some hospitals or clinics within broader hospital and health care networks have implemented different EMR systems. Because each of these EMR systems may use different database types that are distinct and incompatible with one another, accessing records stored in different EMR systems may be difficult. Health care providers wishing to access all records of a single patient may have to search each EMR system separately and compile the results; this process may be time-consuming, difficult, and error-prone.

BRIEF DESCRIPTION OF THE DRAWINGS

The following drawings illustrate particular embodiments and therefore do not limit the scope of the disclosure. The drawings are intended for use in conjunction with the explanations in the following detailed description. Embodiments will hereinafter be described in conjunction with the appended drawings, wherein like numerals denote like elements.

DETAILED DESCRIPTION

The following detailed description is exemplary in nature and is not intended to limit the scope, applicability, or configuration of the disclosure in any way. Rather, the following description provides some practical illustrations for implementing exemplary embodiments. Examples are provided for selected elements, and all other elements employ that which is known to persons of ordinary skill in the art. Persons of ordinary skill in the art will recognize that many of the noted examples have a variety of suitable alternatives.

Certain embodiments disclosed herein describe a system whereby a health care provider may access the records of a single patient or multiple patients, regardless of which EMR system houses the records, and receive results in a standard format that integrates data from multiple sources. Furthermore, whether the objective is to view the integrated output of patient records, use the integrated output for data analysis, or create a visual representation (chart, graph, infographic, etc.) of the integrated output, various embodiments enable these functions.

Figure 1:
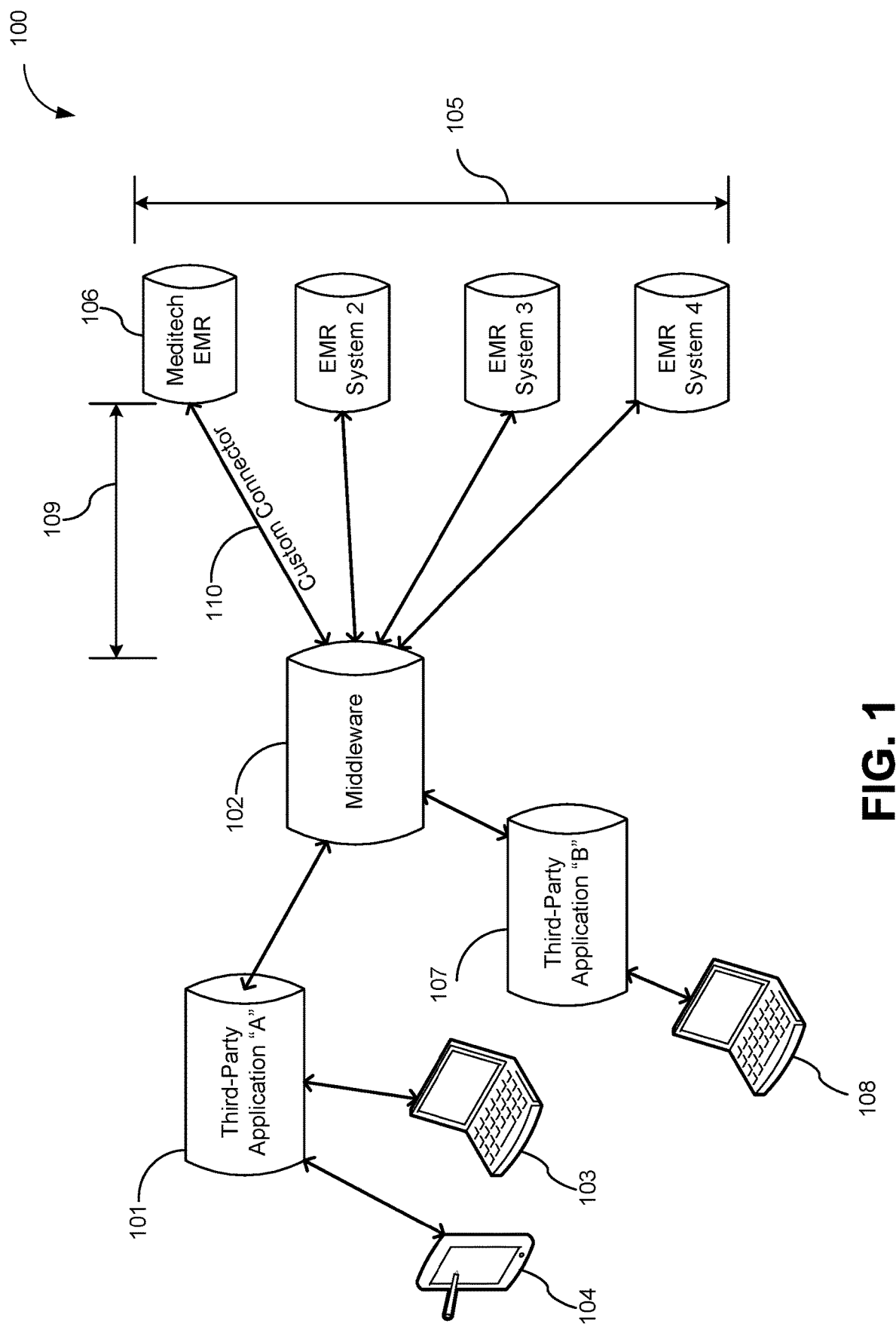
FIG. 1A is a high-level schematic depiction of a system for integrating electronic medical records, according to an embodiment.
FIG. 1B illustrates different connectivity methods that may be used to connect to various EMR systems, according to an embodiment.

FIG. 1A is a high-level schematic depiction of a system 100 for integrating electronic medical records, according to an embodiment. The system 100 includes middleware 102, one or more EMR systems 105, and a third-party application 101 (e.g., software developed and provided separately from middleware 102 and EMR systems 105). The third-party application 101 may be an Internet application, may be hosted by a distinct vendor (unaffiliated with the middleware 102 or EMR systems 105 vendor), and that provides a search interface for authorized users. For example, the third-party application 101 may be an Internet application that presents search options for users on a computer 103 or tablet or smartphone 104.

The third-party application 101 communicates with the middleware 102. In general, the middleware 102 receives a command sent from the third-party application 101, formats the command to be compatible with the targeted EMR system 105, and communicates the formatted command to the targeted EMR system 105. In an embodiment, the EMR systems 105 may comprise more or fewer EMR systems than those illustrated in FIG. 1A, and may or may not include the MEDITECH EMR system 106. The targeted EMR system 105 executes the formatted command, then communicates the execution results to the middleware 102. The middleware 102 takes the execution results received from the EMR system 105 and communicates the execution results to the third-party application 101. The third-party application 101 may transmit the execution results in a user-friendly interface to one or more devices, such as a computer 103 or a tablet or smartphone 104, for display by the one or more devices. The third-party application 101 may modify the execution results prior to transmitting the execution results to the one or more devices.

In an embodiment, the third-party application 101 may perform complex, real-time analytics based on data provided in the execution results from the EMR systems 105 via the middleware 102 and present the analytics to the one or more devices to support clinical decision-making. Although the native functionality of an EMR system 105 may be inconsistent regarding real-time access for some types of data, embodiments may enable a health-care provider to obtain real-time information for all data types consistently. For example, the third-party application 101 may perform calculations based on a complex patient acuity scoring system and transmit the information to a third-party application 101 of a health-care provider. The third-party application 101 may query the middleware 102 to obtain the data necessary to perform the patient acuity calculations, such as vital signs, lab test results, and other information about a patient's condition. Upon receiving the necessary data, the third-party application 101 may perform analytics using the received data and transmit the results to a health-care provider, for example on a tablet or smartphone 104, enabling the health-care provider to view the real-time information (e.g., at a patient's bedside), thereby supporting clinical decision making.

In an embodiment, the middleware 102 may receive commands from multiple third-party applications, such as third-party applications 101 and 107. In an embodiment, a hospital computer 108 that displays a user interface specific to a single EMR system 105 may embed a web viewer capable of connecting to other EMR systems via system 100; this embedded web viewer may be used to retrieve patient information that is located on other EMR systems of the hospital. In such embodiments, the embedded web viewer may communicate with third-party application 107 to send a request to and receive data back from the middleware 102. Upon receipt of the data, the embedded web viewer may display patient information from other EMR systems within the single EMR system, to which the hospital computer 108 is connected.

The middleware 102 may incorporate a connector 109, which may be a web service that facilitates direct, real-time communication with an EMR system 105. The system 100 may have a unique, dedicated connector specific to each EMR system 105. The middleware 102 may also include a custom-built connector 110 to enable real-time communication with the MEDITECH EMR system 106, which does not provide its own connector. This custom-built connector 110 may be the only mechanism for retrieving real-time data from the MEDITECH EMR system 106 in a manner that allows the middleware 102 to standardized exchange of information to support transactions originating from third party applications 101 and 107.

HL7 is a set of international standards for transfer of clinical and administrative data between software applications used by various healthcare providers. Significant differences exist between systems that use middleware 102 and systems that use HL7. Transactions using middleware 102 are request-response based; HL7 transactions are not. HL7 requires the EMR vendor to implement the HL7 standard; systems using middleware 102 do not. An EMR system that implements HL7 will return data in the HL7 standard; middleware 102 returns data that is proprietary to the middleware 102. HL7 does not offer flexible, robust access to the data store of an EMR system 105; thus, third-party vendors that rely on HL7 integration must populate a separate data repository (e.g., a "temporary database"). Existing HL7-based solutions that interact with an EMR system 105 cannot maintain perfect synchronization with the EMR system 105 because they copy data periodically from the EMR system 105 into the temporary database, and then use the temporary database for reading and modifying data. The temporary database reflects data of the EMR system 105 at the time the data was copied; by the time the temporary database is queried or modified, the data may have become stale (e.g., not synchronized) with respect to the data of the EMR system 105. Because the middleware 102 of the disclosed embodiments communicates with the EMR systems 105 in real-time, the middleware 102 operates on data that is identical to the data of the EMR systems 105, and thus system 100 may not need and might not include a temporary database.

The middleware 102 receives real-time data from an EMR system 105 or writes data to an EMR system 105 by communicating with the EMR system 105 in response to commands received from a third-party application 101 or 107. Obtaining real-time data from and writing data in real time to an EMR system 105 may have advantages over existing solutions. First, the system 100 may have a lower risk of data breach because the system 100 does not store data from EMR systems 105. Additionally, existing systems may not provide complete or accurate information. For example, if a patient attended an appointment on a Monday morning and a different health care provider queried that patient's "encounters" using the middleware 102 later that same day, the middleware 102 would retrieve this new data point when it queried the EMR systems 105 and include the data point in the user's results. If the middleware 102 relied instead on a temporary database compiled from all EMR systems 105, the middleware 102 would only retrieve the new data point representing the patient's latest appointment if the middleware 102 queried the temporary database after the temporary database had been updated to include the new data. Patients often have multiple appointments within a short time period, and the schedules for updating a central database may vary; thus, there may be differences or gaps between data in the EMR systems 105 and in the temporary database.

Figure 1B:
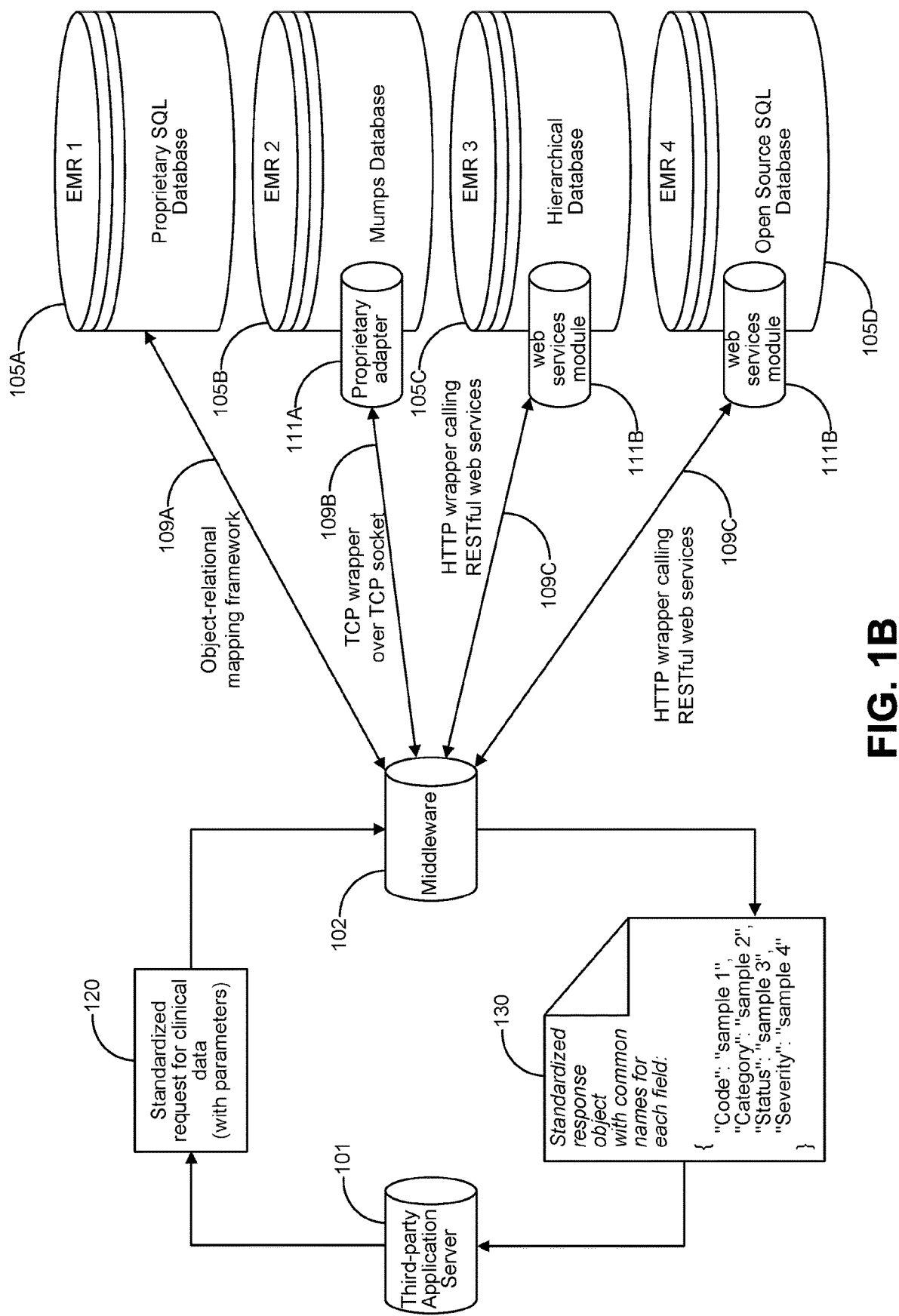

FIG. 1B illustrates different connectivity methods that may be used to connect to various EMR systems 105, according to an embodiment. For example, the middleware 102 may connect to a proprietary SQL database 105A using an object-relational mapping framework 110A, such as LINQ or the Microsoft Entity Framework. In another example, the middleware 102 may connect to a Mumps database 105B using a TCP wrapper over a TCP socket 110B, which connects to a proprietary adapter 111A installed on the Mumps database 105B. The proprietary adapter 111A may listen for TCP packets; when the adapter 111A determines that it has received a request, the adapter 111A may execute commands by invoking another module of the EMR system 105B. In a further example, the middleware 102 may connect to a hierarchical database 105C or an open-source SQL database 105D using an HTTP-wrapper that calls RESTful web services 110C, which connects to a web services module 111B installed on the EMR system 105C, 105D.

Figure 2:
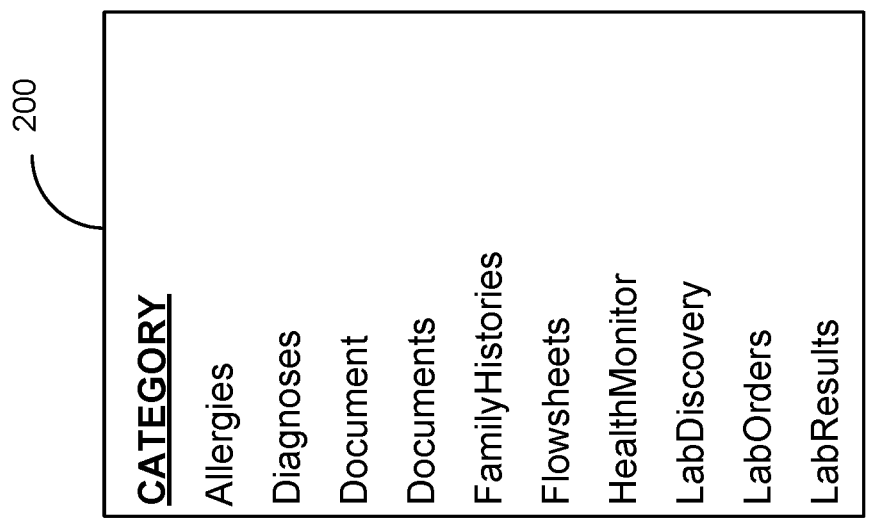
FIG. 2 is an example of a directory of search categories created to assist users, according to an embodiment.

FIG. 2 illustrates a list of categories 200 as they may appear in documentation for middleware 102 of a system 100 for integrating electronic medical records, according to an embodiment. Commands and data elements available in middleware 102 are arranged in categories, such as "allergies" or "diagnoses." Within each category may be commands and data elements related to that category. For example, diabetes is a patient problem that may be listed in the EMR under the category "diagnoses" while a patient visit to a health care provider may be listed under the data element "encounter" within the middleware 102. A user of the system 100 may submit a command for a specific category. The middleware 102 correlates each command from the user to the correct data structure(s) of the EMR system 105. In the example of the category "encounter," the middleware 102 maps "encounter" data and its related commands to the analogous data elements and commands as defined in the databases for each of the EMR systems 105. "Encounter" may correlate to a data element "contact" in one EMR system, and to "visit" in another.

Figure 3A:
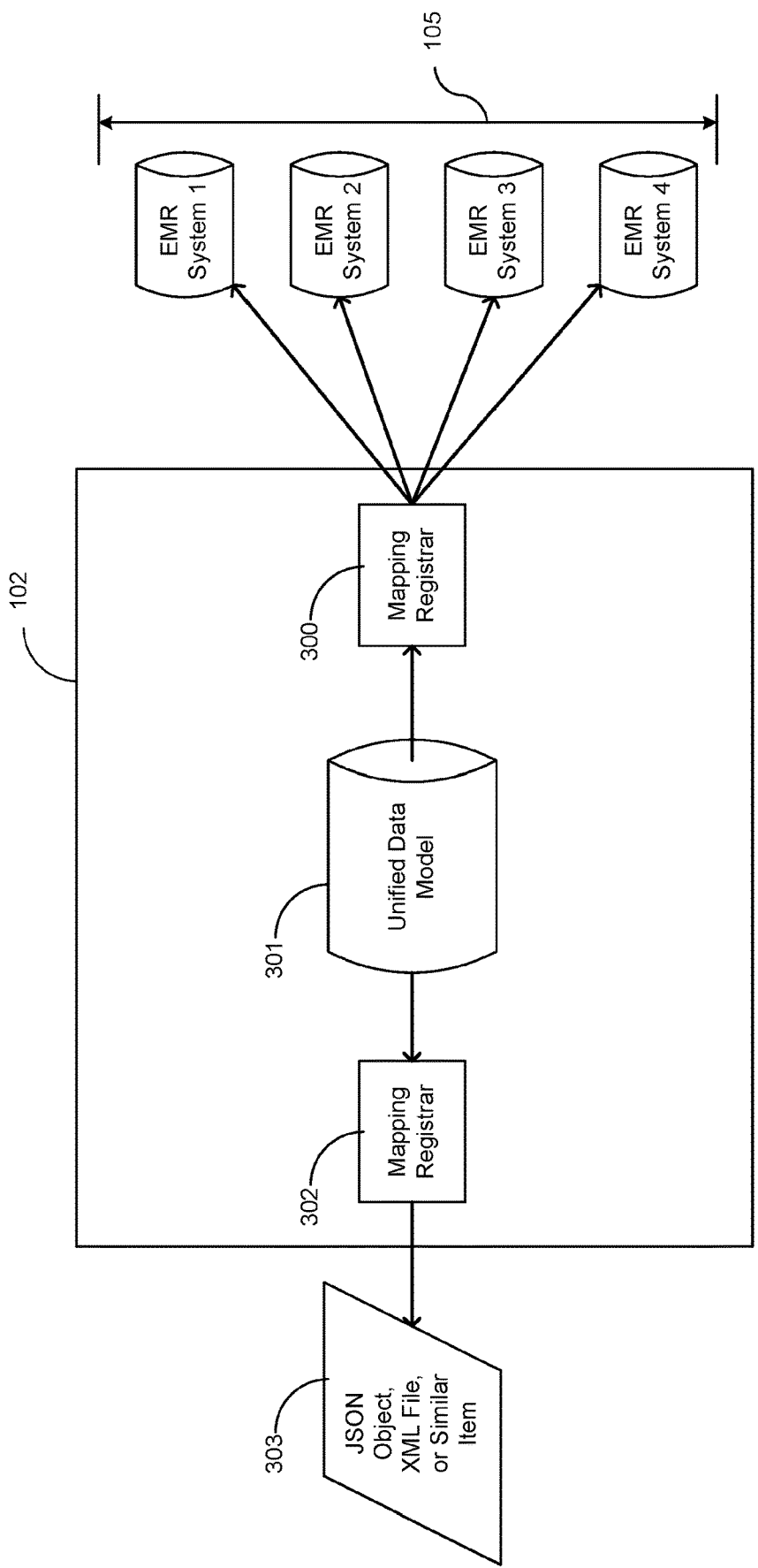
FIG. 3A is a depiction of a process for transferring data received in different formats from various EMR systems into a unified format accessible to users, according to an embodiment.

FIG. 3A is a data flow diagram illustrating mapping registrars 300, 302 within the middleware 102 to convert commands and data elements into formats recognizable by an EMR system 105 and the user of the application system 100, according to an embodiment. Upon the middleware 102 receiving a command from a third-party application 101 or 107, the middleware 102 may use mapping registrar 300 to convert the command into a command recognizable by the EMR system 105 that is to be queried.

In an embodiment, each category in middleware 102 may use a particular application programming interface (API) to accept commands from a third-party application 101 or 107. For example, the table below illustrates an example API that allows a third-party application 101 or 107 to retrieve and/or update, via middleware 102, diagnosis data for a patient in an EMR system. In an embodiment, the parameters may be passed as URI parameters in an HTTP request.

TABLE 1

| Parameter Name | Parameter Description | Parameter Data Type | Additional Information |
|---|---|---|---|
| EMRSystem | The target EMR system. | EMRSystem | Required |
| UserID | Gets or sets the user identifier. | string | Required |
| EncounterID | Gets or sets the encounter identifier. | string | Required |
| PatientID | Gets or sets the patient identifier. | string | None |
| ShowInactive | Gets or sets a value indicating whether to show inactive records. | boolean | None |
| Domain | Gets or sets the domain | string | May be required for certain EMR systems |
| LoginID | Gets or sets the login identifier. | string | May be required for certain EMR systems |
| Password | Gets or sets the password. | string | May be required for certain EMR systems |
| EMRInstance | Gets or sets the EMR instance. | string | None |

FIG. 3A also illustrates the unified data model 301, which represents data converted by mapping registrar 302. To enable a consuming application 101 or 107 to process data elements retrieved from different EMR systems 105 in the same way, data elements that exist in the diverse structures within each EMR system 105 must be provided to the consuming application in standard data structure. The schema of data structures is referred to as the unified data model 301. The middleware 102 translates data received from the EMR systems 105 using a customized mapping registrar 300 into the unified data model 301. In order to return the data within the unified data model 301 to the user in a standard format, the middleware 302 converts the data within the unified data model 301 into a JSON object, an XML file, or another similar response format 303. An example response format 303 is illustrated in the following code.

```
[
    {
        "DiagnosisId": "sample string 1",
        "ClinicalDiagnosis": "sample string 2",
        "PatientId": "sample string 3",
        "EncounterId": "sample string 4",
        "EncounterType": {
            "Id": "sample string 1",
            "Name": "sample string 2"
        },
        "PatientClass": {
            "Id": "sample string 1",
            "Name": "sample string 2"
        },
        "Concept Source": "sample string 5",
        "SourceVocabulary": "sample string 6",
```

```
        "ConfirmationStatus": "sample string 7",
        "DiagnosisDateTime": "2016-09- 30120: 16:30. 60170862",
        "Classification": "sample string 8",
        "DiagnosisType": "sample string 9",
        "AdmitDiagnosis": true,
        "Severity": "sample string 10",
        "DiagnosisProvider": "sample string 11",
        "ActiveInd": true,
        "DiagnosisCode": "sample string 12",
        "ICD9": "sample string 13",
        "ICD10": "sample string 14",
        "SNOMED": "sample string 15"
    },
    {
        "DiagnosisId": "sample string 1",
        "ClinicalDiagnosis": "sample string 2",
        "PatientId": "sample string 3",
        "EncounterId": "sample string 4",
        "EncounterType": {
            "Id": "sample string 1",
            ...
]
```

Figure 3B:
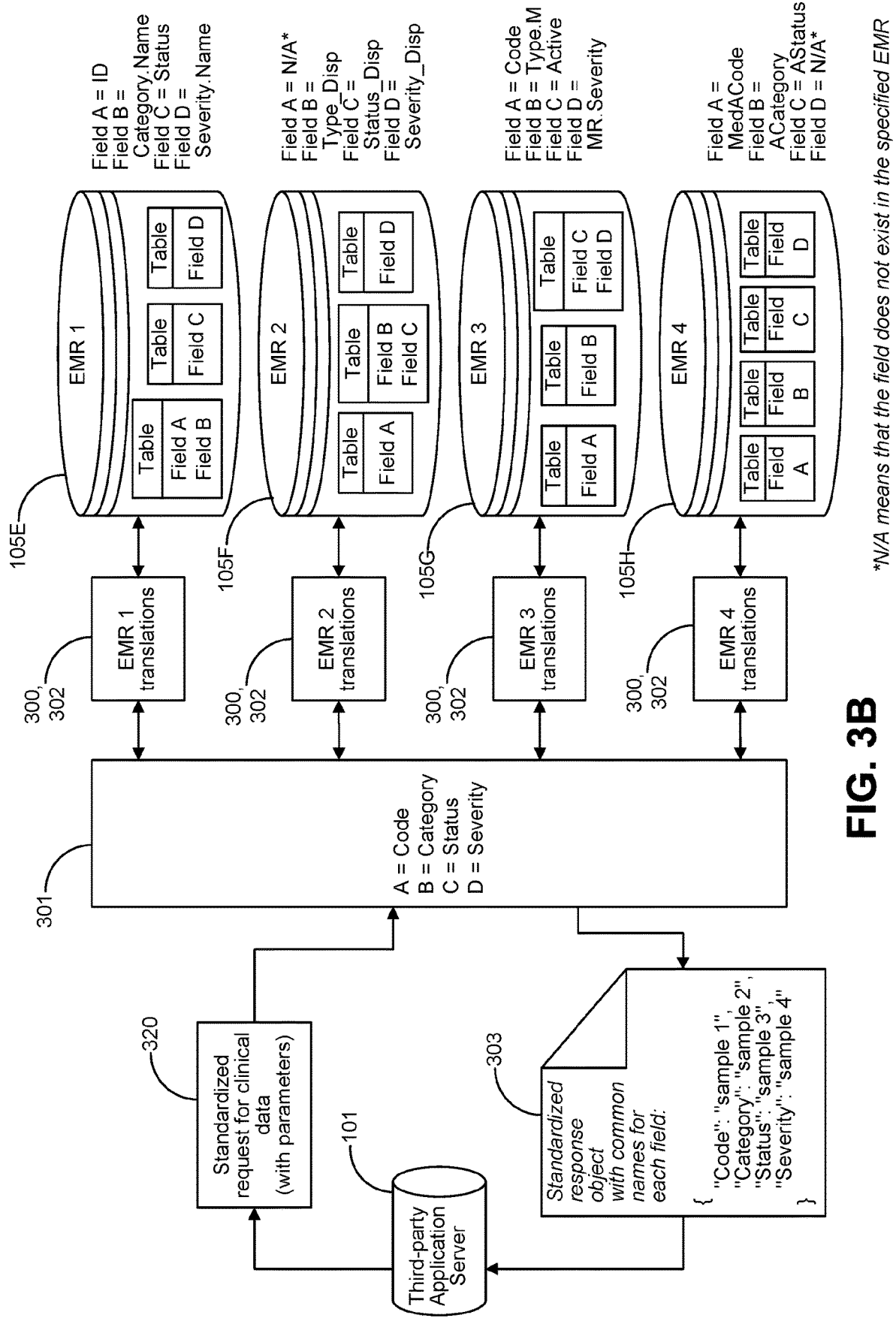
FIG. 3B is an illustration of a unified data model mapping for a clinical indicator, according to an embodiment.

FIG. 3B is an illustration of a unified data model mapping for a clinical indicator, according to an embodiment. Each EMR system 105E-H uses a data schema; the unified data model enables mapping of similar data elements across disparate EMR schemas. The unified data model 301 also enables mapping of data elements that are named differently in different EMR schemas, and enables mapping of data elements that do not exist in a schema.

The unified data model 301 only includes data elements that are available in one or more EMR systems 105E-H. If the EMR system 105 queried contains no defined corollary to a given data element, a query of that EMR system 105 for the data element will return no results. For example, if a user queries the system 100 for laboratory orders or results, a query of an EMR system 105 that contains no data element correlated to the data element "LOINC Code" (a standardized nomenclature for clinical and laboratory observations) will return no results.

Figure 4:
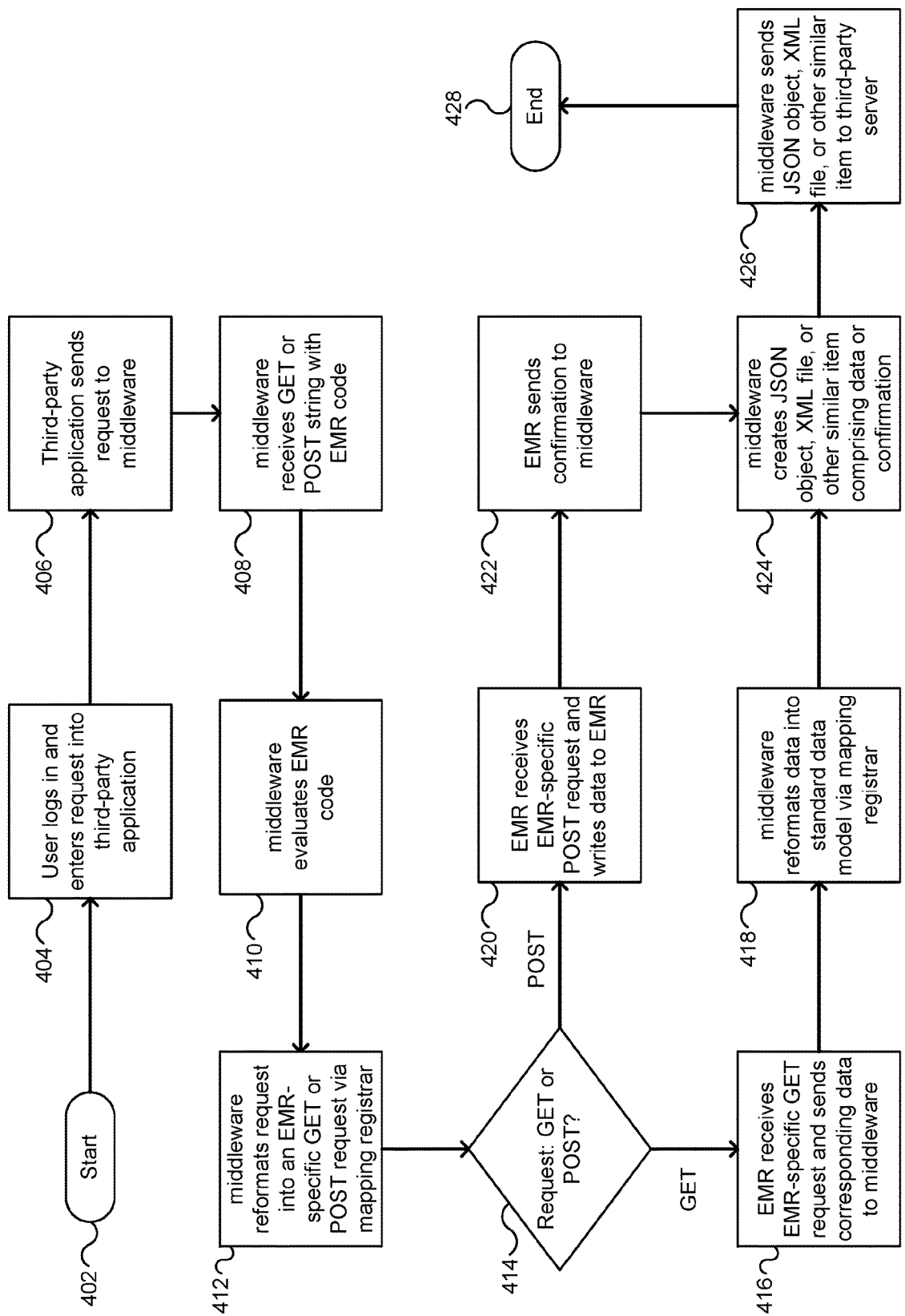
FIG. 4 is a flowchart of a method for querying multiple EMR systems and integrating the results from the queried EMR systems into an integrated output, according to an embodiment.

FIG. 4 is a flowchart of a method of querying an EMR system 105 and integrating the results from the queried EMR system 105 into an integrated output, according to an embodiment. At 402, the user may initiate a command by logging into an interface presented by the third-party application 101 or 107. The third-party application 101 or 107 may perform an accuracy check on the user's ID and password before permitting the user to access information.

At 404, once logged in, the user may select a patient and retrieve the appropriate patient ID or ID of a patient list where such list includes multiple patient IDs (such as all admitted patients in a specific unit of a specific hospital). EMR systems 105 may be queried for information attributable to a specific patient ID or patient list, thus, commands sent to the middleware 102 by third-party application 101 or 107 may include a patient ID or patient list ID. Queries sent to one or more data categories provided by the middleware 102 may provide patient data for multiple patients on the patient list.

A user may submit a command into the interface of the third-party application 101 or 107. The command may include a user ID and password, a patient ID or a patient list ID, the target EMR system 105, and a request to read, write, update, or delete data. In an embodiment, a request sent by the third-party application 101 or 107 is independent, stateless, and specifies the target EMR system. After the user inputs the data into the interface of the third party application 101 or 107, the third-party application 101 or 107 may transform the command into an appropriate string for retrieving, editing, or adding new data, and then may communicate the string to the middleware 102 (operation 406). The communication may be performed using one or more of a variety of communications protocols, such as Hypertext Transfer Protocol (HTTP); if HTTP is used, the GET string may be transmitted using the HTTP GET method and the POST string may be transmitted using the HTTP POST method.

The middleware 102 may receive the string representing the command from the third-party application 101 or 107 (operation 408). The middleware 102 may evaluate the string to determine which of the EMR systems 105 was specified (operation 410). The middleware 102 may reformat, using mapping registrar 300, the command within the string so that the reformatted command is compatible with the specified EMR system 105 (operation 412).

The middleware 102 may send the reformatted command directly to the specified EMR system 105 via the connector 109 that corresponds to the specified EMR system 105. The specified EMR system 105 may receive the reformatted command and may take action(s) according to whether the reformatted command included a retrieve, edit, or add request (operation 414). If the reformatted command included a retrieval request, the EMR system 105 may send a response to the middleware 102 (operation 416). The middleware may then 102 translate, using customized mapping registrar 302, the responses received from the EMR system 105 into the unified data model 301. If the reformatted command included an add, new, or edit request, the EMR system 105 may write data to the EMR system 105 (operation 420). The EMR system 105 may send a confirmation to the middleware 102 (operation 422). Regardless of whether the reformatted command included a retrieval request or an add/edit request, the middleware 102 may package the reformatted data or confirmation into a JSON object, an XML file, or another similar item 303 (operation 424).

The middleware 102 may transmit the JSON object or XML file 303 to the third-party application 101 or 107 (operation 426). For example, if the user queried scanned document images for a particular patient ID, the JSON object or XML file 303 may include an array of those images. The JSON object or XML file 303 is in a format that is accessible via the user interface available on the third-party application 101 or 107. Because the system 100 operates using real-time communications, the middleware 102 does not store any of the data retrieved from the EMR system 105, including the JSON object or XML file 303.

The invention claimed is:

1. A method performed by a middleware application, the method comprising:
receiving, by the middleware application via a first electronic network, a command from a third-party application, the command conforming to a unified data format specified by a unified data model, the command to include at least one of:
a request to retrieve data from a first electronic medical records (EMR) system of a plurality of EMR systems; and
a request to write data to the first EMR system of the plurality EMR systems,
wherein the middleware application is configured to communicate with each of the plurality of EMR systems, and wherein the first EMR system of the plurality of EMR systems and a second EMR system of the plurality of EMR systems are compatible with different data formats;
converting, by the middleware application and using a first mapping registrar, the command into a data format compatible with the first EMR system, wherein the first mapping registrar maps data elements in the command from the unified data format to data elements in the data format compatible with the first EMR system;
transmitting, by the middleware application via a second electronic network, the converted command to the first EMR system;
receiving, by the middleware application via the second electronic network, a response from the first EMR system, wherein the response is in the data format compatible with the first EMR system; and
converting, by the middleware application and using a second mapping registrar different than the first mapping registrar, the response into a result conforming to the unified data format, wherein the second mapping registrar maps data elements in the response from the data format compatible with the first EMR system to data elements in the unified data model.

2. The method of claim 1, further comprising:
transmitting, by the middleware application via the first electronic network, the converted result to the third-party application.

3. The method of claim 1, wherein transmitting the formatted command to the EMR system is performed by calling a connector application that facilitates direct communication with the EMR system.

4. The method of claim 3, wherein the connector application is a web service application.

5. The method of claim 1, wherein the formatted result is a JavaScript Object Notation (JSON) object.

6. The method of claim 1, wherein the formatted result is an XML file.

7. The method of claim 1, wherein the received command is received by the middleware application as one of:
a Hypertext Transfer Protocol (HTTP) GET method;
a HTTP PUT method;
a HTTP DELETE method; and
a HTTP POST method.

8. A system, comprising:
a middleware application configured to:
communicate with each of a plurality of electronic medical records (EMR) systems, and wherein a first EMR system of the plurality of EMR systems and a second EMR system of the plurality of EMR systems are compatible with different data formats
receive, via a first electronic network, a command from a third-party application, the command in conformance to a unified data format specified by a unified data model, the command to include at least one of:
a request to retrieve data from the first EMR system of the plurality of EMR systems; and
a request to write data to the first EMR system of the plurality EMR systems;
convert, using a first mapping registrar, the command into a data format compatible with the first EMR system, wherein the first mapping registrar maps data elements in the command from the unified data format to data elements in the data format compatible with the first EMR system;
transmit, via a second electronic network, the converted command to the first EMR system;

receive, via the second electronic network, a response from the first EMR system, wherein the response is in the data format compatible with the first EMR system; and convert, using a second mapping registrar different than the first mapping registrar, the response into a result conforming to the unified data format, wherein the second mapping registrar maps data elements in the response from the data format compatible with the first EMR system to data elements in the unified data model.

9. The system of claim 8, further comprising:
the middleware application configured to transmit, via the first electronic network, the converted result to the third-party application.

10. The system of claim 8, wherein transmission of the formatted command to the EMR system is performed by calling a connector application that facilitates direct communication with the EMR system.

11. The system of claim 10, wherein the connector application is a web service application.

12. The system of claim 8, wherein the formatted result is a JavaScript Object Notation (JSON) object.

13. The system of claim 8, wherein the formatted result is an XML file.

14. The system of claim 8, wherein the received command is received by the middleware application as one of:
a Hypertext Transfer Protocol (HTTP) GET method;
a HTTP PUT method;
a HTTP DELETE method; and
a HTTP POST method.

15. A non-transitory computer-readable medium including instructions that, when executed by a processor of a computer, causes the computer to:
receive, by a middleware application via a first electronic network, a command from a third-party application, the command in conformance to a unified data format specified by a unified data model, the command to include at least one of:
a request to retrieve data from a first electronic medical records (EMR) system of a plurality of EMR systems; and
a request to write data to the first EMR system of the plurality EMR systems,
wherein the middleware application is configured to communicate with each of the plurality of EMR systems, and wherein the first EMR system of the plurality of EMR systems and a second EMR system of the plurality of EMR systems are compatible with different data formats;

convert, by the middleware application and using a first mapping registrar, the command into a data format compatible with the first EMR system, wherein the first mapping registrar maps data elements in the command from the unified data format to data elements in the data format compatible with the first EMR system;

transmit, by the middleware application via a second electronic network, the converted command to the first EMR system;

receive, by the middleware application via the second electronic network, a response from the first EMR system, wherein the response is in the data format compatible with the first EMR system; and convert, by the middleware application and using a second mapping registrar different than the first mapping registrar, the response into a result conforming to the unified data format, wherein the second mapping registrar maps data elements in the response from the data format compatible with the first EMR system to data elements in the unified data model.

16. The non-transitory computer-readable medium of claim 15, further including instructions that, when executed by a processor of a computer, causes the computer to:
transmit, by the middleware application via the first electronic network, the converted result to the third-party application.

17. The non-transitory computer-readable medium of claim 15, wherein transmission of the formatted command to the EMR system is to be performed by calling a connector application that facilitates direct communication with the EMR system.

18. The non-transitory computer-readable medium of claim 17, wherein the connector application is a web service application.

19. The non-transitory computer-readable medium of claim 15, wherein the formatted result is a JavaScript Object Notation (JSON) object.

20. The non-transitory computer-readable medium of claim 15, wherein the formatted result is an XML file.

21. The non-transitory computer-readable medium of claim 15, wherein the received command is received by the middleware application as one of:
a Hypertext Transfer Protocol (HTTP) GET method;
a HTTP PUT method;
a HTTP DELETE method; and
a HTTP POST method.

* * * * *